(12) United States Patent
Burgess et al.

(10) Patent No.: US 6,362,216 B1
(45) Date of Patent: Mar. 26, 2002

(54) COMPOUNDS WHICH INHIBIT TRYPTASE ACTIVITY

(75) Inventors: Laurence E. Burgess, Boulder; James P. Rizzi, Niwot, both of CO (US)

(73) Assignee: Array Biopharma Inc., Boulder, CO (US)

( * ) Notice: Subject to any disclaimer, the term of this patent is extended or adjusted under 35 U.S.C. 154(b) by 0 days.

(21) Appl. No.: 09/563,981

(22) Filed: May 3, 2000

Related U.S. Application Data

(63) Continuation of application No. 09/179,695, filed on Oct. 27, 1998, now abandoned.

(51) Int. Cl.$^7$ .................... A61K 31/381; C07D 333/60
(52) U.S. Cl. ..................... 514/443; 549/57; 549/58
(58) Field of Search ................ 549/57, 58; 514/443

(56) References Cited

U.S. PATENT DOCUMENTS

| | | | |
|---|---|---|---|
| 3,598,839 A | 8/1971 | Kaltenbronn | 514/443 |
| 4,665,206 A | 5/1987 | Redpath et al. | 549/51 |
| 4,668,697 A | 5/1987 | Shepard et al. | 514/443 |
| 4,888,432 A | 12/1989 | Hamprecht | 549/57 |
| 5,481,021 A | 1/1996 | Garland et al. | 560/35 |
| 5,525,623 A | 6/1996 | Spear et al. | 514/423 |
| 5,886,191 A | 3/1999 | Dominguez et al. | 598/491 |

FOREIGN PATENT DOCUMENTS

| | | |
|---|---|---|
| DE | 3427 865 A1 | 2/1986 |
| DE | 4128871 * | 3/1993 |
| EP | 0 048 433 A2 | 3/1982 |
| EP | 0 540 051 A1 | 5/1993 |
| EP | 0 556 024 A1 | 8/1993 |
| EP | 0 802 179 A1 | 10/1997 |
| WO | WO 94/27958 | 12/1994 |
| WO | WO 96/09297 | 3/1996 |
| WO | WO 97/37969 | 10/1997 |
| WO | WO 98/01428 | 1/1998 |

OTHER PUBLICATIONS

International Search Report in Application No. PCT/US98/23362 dated Feb. 12, 1999.
"The Merck Index, 9$^{th}$ edition" 1976, Merck & Co., Inc. Rahway, N.J. XP002093171.
Fairley, T.A., et al., 'Structure, DNA minor groove binding, and base pair specificity of alkyl– and aryl–linded bis(amidinobenzimidazoles) and bis(amidinoindoles), ' *J. Med. Chem.* 36: 1746–1753 (1993).
Balzarini, J., et al., Invest. New Drugs, "Inhibitory activity of diarylamidine derivatives on murine leukemia L1210 cell growth," *Invest. New Drugs*, 1(2), pp. 103–115, 1983.
Anné, J., et al., "Antifungal and antibacterial activities of diarylamidine derivatives," *Antimicrob. Agents Chemother.*, 18(2), pp. 231–239, 1980.
De Clercq et al., "Diaryl amidine derivatives as oncornaviral DNA polymerase inhibitors," *J. Med. Chem.*, 23(7), p. 788, 1980.
Kano et al., CA 99:175648, 1983.
Sugimoto et al., CA 110:134863, 1989.

* cited by examiner

*Primary Examiner*—Laura L. Stockton
(74) *Attorney, Agent, or Firm*—McDonnell Boehnen Hulbert & Berghoff

(57) ABSTRACT

The present invention is directed to compounds which are capable of inhibiting the activity of tryptase. Such compounds are useful in the treatment or prevention of inflammatory disease, particularly those disease states which are mediated by mast cell activation. Also encompassed by the invention are formulations comprising the noted compounds, processes for preparing such compounds and methods for treating or preventing an inflammatory disease.

12 Claims, No Drawings

COMPOUNDS WHICH INHIBIT TRYPTASE ACTIVITY

This application is a continuation of U.S. patent application Ser. No. 09/179,695, filed Oct. 27, 1998 now abandoned.

FIELD OF THE INVENTION

This invention relates to anti-inflammatory and anti-allergy agents and, more particularly, relates to novel compounds, formulations and methods for the prophylaxis and treatment of inflammation, allergy and pulmonary disorders. The invention particularly relates to compositions and methods that are efficacious for the treatment of tryptase-related and mast cell mediated inflammatory disorders.

BACKGROUND OF THE INVENTION

The disorders noted above include, among others, asthma and other inflammatory diseases of the pulmonary system like allergic rhinitis, chronic obstructive pulmonary disease, respiratory syncytial virus and smoker's emphysema where the methods and compositions described herein are useful. Furthermore, the compositions and methods are particularly useful in treating the underlying pathological changes in the airways associated with these diseases such as basement membrane thickening, cell hypertrophy and hyperplasia, inflammatory cell influx, and other tissue remodeling. Other inflammatory conditions, including, for example, rheumatoid arthritis, multiple sclerosis, inflammatory bowel disease, conjunctivitis, psoriasis, scleroderma, and related diseases can be treated with the compounds and methods described herein.

To better understand the invention, the following brief description of mast cell mediated disease, particularly asthma, is provided. Human asthma is a complex inflammatory disease. Genetic susceptibility and repeated allergen exposure from a variety of sources lead to allergen sensitization that, via IL-4 production from T-cells and mast cells, can ultimately induce B-cell derived IgE levels that are significantly elevated over normal levels. Subsequent exposure to allergen coupled with these newly elevated IgE levels can activate the Fc&RI high affinity IgE receptor on the surface of mast cells and other pro-inflammatory cells in the lung to induce degranulation/activation and thus trigger a cascade of inflammatory responses. This early phase of the response is characterized by severe bronchoconstriction that reaches its peak at about 15 minutes followed by a recovery of several hours. Many pre-formed substances are immediately released from the mast cell including histamine, heparin, cytokines (including, for example, IL-3, IL-4, IL-5, IL-6, and TNF-α), and proteases (including, for example, cathepsin G, chymase, carboxy peptidase A, tryptase). In relation to these other proteases, tryptase is released in very large amounts—up to 35 pg per cell (see Caughey, *Am. J. Physiol.*, 257, L39–46 (1989) and Walls in "Asthma and Rhinitis" 1995, pp. 801–824). Furthermore, tryptase is long lived, and has been shown to have a myriad of significant effects as a peptidase, protease and cytokine that intensify the inflammatory response. For example, tryptase can cause further mast cell degranulation to amplify the allergen response (see Molinari et al., *J. Appl. Physiol.*, 79(6), 1966–70 (1995)) and induce eosinophil and neutrophil migration into the lung (see Walls et al., *Int. Arch. Allergy Immunol.*, 107, 372–3 (1995)). Also, tryptase can inactivate fibrinogen to act as a local anti-coagulant and promotes plasma extravasation bringing more circulating cells and mediators into the lung (see Schwartz et al, *J. Immunol.*, 135, 2762–7 (1985)). Further, tryptase can process high and low molecular weight kininogen to bradykinin and activates kallikrein to produce neurogenic inflammation (see Proud et al., *Biochem. Pharm.*, 37(8), 1473–80 (1988); Walls et al., *Biochem. Soc. Trans.*, 20, 260S (1992); Imamura et al., *Lab. Invest.*, 74, 861–70 (1996)) while degrading neurogenic feedback mechanisms like the bronchodilatory neuropeptides (for example, VIP, peptide histidine methionine and peptide histidine isoleucine) and further promote mucous secretion and broncho-constriction (see Tam and Caughey, *Am. J. Respir. Cell Mol. Biol.*, 3, 27–32 (1990)). Tryptase can amplify the effects of histamine to further enhance bronchoconstriction (see Molinari et al., *J. Appl. Physiol.*, 79(6), 1966–70 (1995); Sekizawa et al., *J. Clin. Invest.*, 83, 175–9 (1989); Johnson et al., *Eur. Respir. J.*, 10, 38–43 (1997)). Tryptase is a mitogen/activator of fibroblast (see Ruoss et al., *J. Clin. Invest.*, 88, 493–9 (1991); Gruber et al., *J. Immunology*, 158, 2310–17 (1997)) and bronchial smooth muscle cells which can contribute to airway hyperresponsiveness to the lung as seen in a variety of pulmonary disorders (see Brown et al., *Chest*, 107(3), 95–6S (1995); Caughey et al., *Am. J. Respir. Cell Mol. Biol.*, 13, 227–36 (1995)). Further, tryptase is a mitogen for airway epithelial cells and induces IL-8 and ICAM-1 expression (see Cairns and Walls *J. Immunology*, 156, 275–83 (1996)) and recently tryptase has been shown to activate cellular receptors (see Molino et al., *J. Biol. Chem.*, 272(7), 4043–49 (1997)).

Following this early mast cell degranulation and release of tryptase, the activation of the arachidonic acid cascade resulting in the production of lipid mediators, such as the leukotrienes (LTD4, LTC4, LTE4, LTB4), the prostaglandins (PGD2) and platelet activating factor (PAF), occurs several minutes later. Six to twelve hours after initial allergen exposure, a late phase inflammatory response takes place in which bronchoconstriction is again visited upon the asthmatic. By this time the mast cell has begun to produce protein mediators like the cytokines (IL-1,3,4,5,6), chemokines (IL-8, MIP-1a) and growth factors (GM-CSF). This late phase response is associated with a significant influx of inflammatory cells, most notably eosinophils, neutrophils, and lymphocytes, into the lung tissue and airway space. These cells are activated and release even more mediators which can contribute to the significant tissue damage and development of hyperresponsiveness seen in chronic asthma.

The various activities of tryptase contribute to the early and late phase bronchoconstriction as well as to the development of airway hyperresponsiveness, a hallmark of asthma. Furthermore, in chronic asthma and other long term respiratory diseases, these activities cause profound changes to the airway such as desquamation of the epithelial lining, fibrosis and thickening of the underlying tissues. These changes are not treated by present therapeutics.

Tryptase can be detected in a variety of biological fluids and recently tryptase's relatively long biological half-life (vis à vis histamine) has become appreciated and clinicians now use circulating levels of tryptase as a marker of anaphylaxis (see Schwartz et al., *N. Engl. J. Med.*, 316, 1622–26 (1987)). Elevated levels of tryptase can be detected in lavage fluid from allergen challenged atopic asthmatics as well as in cigarette smokers, where there is significant lung damage (see Castells et al., *J. Allerg. Clin. Immunol.*, 82, 348–55 (1988); Wenzel et al., *Am. Rev. Resp. Dis.*, 141, 563–8 (1988); Kalenderian et al., *Chest*, 94, 119–23 (1988)).

Tryptase can process prostromelysin to mature stromelysin (MMP-3) which can further activate collagenase (MMP-1). Thus tryptase could play a significant role in the tissue remodeling of various pulmonary disorders (most notably asthma) but also in rheumatoid and osteo-arthritis.

Tryptase is stored in the mature form as a homotetramer within the secretory granules of the mast cell and probably is held in an inactivated form by the low pH of this intracellular media. When released it is stabilized by interactions with heparin. This unique assembly of 4 catalytically active subunits could also be considered to be a dimer of dimers because computational models indicate that two adjacent active sites may face one another.

Being a member of the tryptic-like serine protease family, human tryptase prefers an arginine or lysine in the P1 subsite of a substrate. Because of this well recognized preference for basic residues at S1 there have been reports of inhibitors that incorporate physiologically protonated basic chemical moieties. (See, for example, benzamidines (see Caughey et al., *J. Pharm. Exp. Therap.*, 264, 676–82 (1993); Tidwell, et al., *J. Med. Chem.* 21(7), 613 (1978); Dominguez et al., WO 9801428 and references cited therein); benzguanidines, benzylamines (see Rice et al., WO 9609297); and, modified peptides incorporating an arginine (see Spear et al., WO 9420527)). (See also Lum, et al., WO 95/32945 (based on U.S. Ser. No. 08/252,099, filed Jun. 1, 1994, now issued as U.S. Pat. No. 5,656,660 (granted Aug. 12, 1997)); Neises et al., U.S. Pat. No. 5,391,705 (granted Feb. 21, 1995); Neises et al., U.S. Pat. No. 5,498,779 (granted Mar. 12, 1996); Neises et al. EP A 0504064 (published Sep. 16, 1992); Powers et al., U.S. Pat. No. 4,954,519 (granted Sep. 4, 1990); Von der Saal et al., WO 94/27958 (published Dec. 8, 1994) and Spear et al., U.S. Pat. No. 5,525,623 (granted Jun. 11, 1996)); .

SUMMARY OF THE INVENTION

As noted, the present invention provides novel compounds which inhibit tryptase activity. Also provided are formulations containing the novel compounds and methods of using the compounds to treat a patient in need thereof. More specifically, there are provided methods for the treatment of a patient suffering from a mast cell mediated disorder, including for example, asthma, allergic rhinitis, rheumatoid arthritis, dermatological diseases, multiple sclerosis, conjunctivitis, inflammatory bowel disease, anaphylaxis, osteoarthritis, peptic ulcers, cardiovascular disease, or other disease state in which mast cells and, in particular, tryptase activation is involved. In addition, there are described processes for preparing the inhibitory compounds of the invention.

The present invention relates to tryptase inhibitors, pharmaceutically acceptable salts and prodrugs thereof useful in the treatment or prophylaxis of inflammatory diseases, particularly asthma and other related inflammatory diseases. The invention also encompasses pharmaceutical compositions and methods for prophylaxis and treatment of asthma, pulmonary disorders and related inflammatory, mast-cell mediated diseases, particularly those which involve activation of tryptase. Also provided are processes for making such compounds as well as intermediates useful in such processes.

DETAILED DESCRIPTION OF THE INVENTION

As noted, the present invention provides compounds useful for the treatment or prophylaxis of inflammatory diseases. In particular, a compound of Formula (I):

(I)

wherein
X is —C(O)—, —(CH$_2$)$_n$— or —SO$_2$—;
R is —H, straight or branched chain(C$_1$–C$_6$)-alkyl, —(C$_3$–C$_8$)-cycloalkyl or —(CH$_2$)$_m$—Ar'—(Y)$_t$;
Ar or Ar' is aryl, heteroaryl, or a 5-membered to 7-membered carbocyclic or heterocyclic ring;
Y is R$^1$HN—C(=NH)—, R$^1$HN—CO—NH—, N≡C— or R$^1$HN—(CH$_2$)$_y$—, (C$_1$–C$_6$) alkyl-SO$_2$NH—, —SO$_2$NH$_2$, (C$_1$–C$_6$) alkyl-CONH—, —OH, —SH, —CF$_3$, —F, —Cl, —Br, —I, —H, —O(C$_1$–C$_6$) alkyl, aryl, —(C$_1$–C$_6$) alkylaryl, heteroaryl, (C$_1$–C$_6$) acyloxy, (C$_1$–C$_6$) alkyl, (C$_1$–C$_6$) alkylthio, —NO$_2$;
R$^1$ is —H, (C$_1$–C$_4$) alkyl-O—CO—, (C$_1$–C$_4$)alkyl-O— or HO—;
j is an integer from 1 to 5, inclusive;
n is an integer between 0 and 10, inclusive;
m is an integer between 0 and 10, inclusive;
t is an integer from 1 to 5, inclusive;
v is an integer between 0 and 6, inclusive;
wherein which each Y, Ar, or Ar', is the same or different, provided that if X is —C(O)—, then n is not zero; or, a pharmaceutically acceptable salt, ester, or solvate thereof, is useful for the treatment or prophylaxis of an inflammatory disease, particularly a mast-cell mediated inflammatory disease, especially one in which tryptase is activated.

Preferred compounds of Formula (I) are those in which Ar and Ar' are independently, phenyl, indole, naphthalene, benzothiophene, or benzimidazole, and in which Y is R$^1$HN—C(=NH)—.

The term "alkyl" refers to a univalent saturated, straight- or branched-chain alkyl group containing the designated number of carbon atoms. Thus, the term "C$_1$–C$_6$ alkyl" refers to a univalent saturated, straight- or branched-chain alkyl group which can contain from one to six carbon atoms, for example, methyl, ethyl, n-propyl, isopropyl, n-butyl, sec-butyl, t-butyl, n-pentyl, 2-methylbutyl, 3-methylbutyl, n-hexyl, 2-methylpentyl, 3-methylpentyl, 4-methylpentyl, 2,2-dimethylbutyl, 2,3-dimethylbutyl, and the like.

The term alkoxy refers to an alkyl group bonded through an oxygen atom to another substituent. Thus, the term "C$_1$–C$_4$ alkoxy" refers to a C$_1$–C$_4$ alkyl group bonded through an oxygen atom to another substituent and includes, for example, methoxy, ethoxy, n-propoxy, n-butoxy, t-butoxy and isobutoxy.

The term "carbocyclic" refers to an organic cyclic moiety in which the cyclic skeleton is comprised of only carbon atoms whereas the term "heterocyclic" refers to an organic cyclic moiety in which the cyclic skeleton contains one or more heteroatoms selected from nitrogen, oxygen, or sulfur and which may or may not include carbon atoms.

Thus, the term "cycloalkyl" refers to a carbocyclic moiety containing the indicated number of carbon atoms. The term "C$_3$–C$_8$ cycloalkyl", therefore, refers to an organic cyclic substituent in which three to eight carbon atoms form a three, four, five, or six, seven, or eight-membered ring, including preferably, for example, a cyclopropyl, cyclobutyl, cyclopentyl, or cyclohexyl ring.

"Aryl" refers to an aromatic carbocyclic group having a single ring, for example, a phenyl ring, multiple rings, for example, biphenyl, or multiple condensed rings in which at least one ring is aromatic, for example, naphthyl, 1,2,3,4,-tetrahydronaphthyl, anthryl, or phenanthryl, which can be unsubstituted or substituted with one or more substituents selected from halogen, lower (C$_1$–C$_4$) alkyl, lower (C$_1$–C$_4$) alkoxy, lower (C$_1$–C$_4$) alkylthio, trifluoromethyl, lower ($C_1$–$C_4$) acyloxy, aryl, heteroaryl and hydroxy. The substituents attached to a phenyl ring portion of an aryl moiety (i.e. either or both of Ar or Ar') in the compounds of Formula (I) may be configured in the ortho-, meta- or para-orientations, with the meta- and para-orientations being preferred.

Examples of typical aryl moieties included in the scope of the present invention may include, but are not limited to, the following:

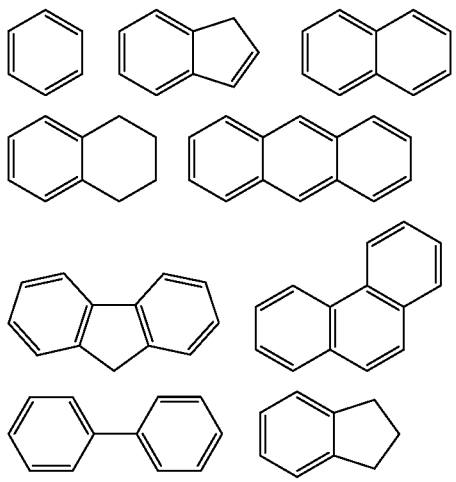

"Heterocycle" or "heterocyclic" refers to a saturated, unsaturated or aromatic carbocyclic group having a single ring, multiple rings or multiple condensed rings, and having at least one hetero atom such as nitrogen, oxygen or sulfur within at least one of the rings. "Heteroaryl" refers to a heterocycle in which at least one ring is aromatic. Any of the heterocyclic or heteroaryl groups can be unsubstituted or optionally substituted with one or more groups selected from halogen, lower ($C_1$–$C_4$) alkyl, lower ($C_1$–$C_4$) alkoxy, lower ($C_1$–$C_4$) alkythio, trifluoromethyl, lower ($C_1$–$C_4$) acyloxy, and hydroxy.

As one skilled in the art will appreciate such heterocyclic moieties may exist in several isomeric forms, all of which are to be encompassed by the present invention. For example, a 1,3,5-triazine moiety is isomeric to a 1,2,4-triazine group. Such positional isomers are to be considered within the scope of the present invention. Likewise, the heterocyclic or heteroaryl groups can be bonded to other moieties in the compounds of the invention. The point(s) of attachment to these other moieties is not to be construed as limiting on the scope of the invention. Thus, by way of example, a pyridyl moiety may be bound to other groups through the 2-, 3-, or 4-position of the pyridyl group. All such configurations are to be construed as within the scope of the present invention.

Examples of heterocyclic or heteroaryl moieties included in the scope of the present invention may include, but are not limited to, the following:

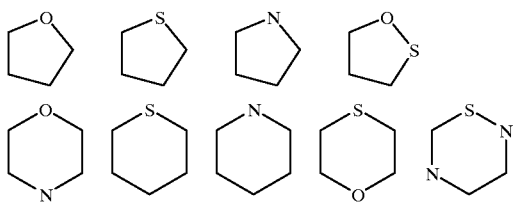

-continued

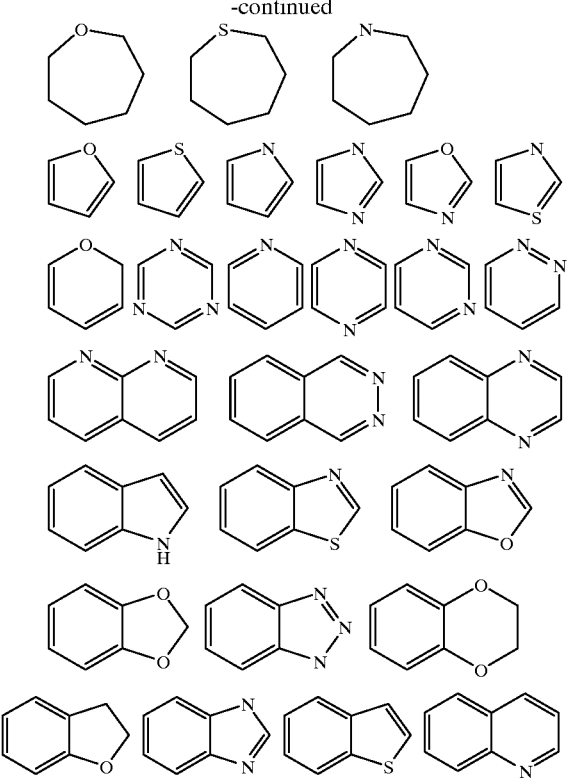

The term "halo" refers to a halogen atom which may include fluoro, chloro, bromo and iodo. Preferred halo groups include chloro, bromo and fluoro with chloro and fluoro being especially preferred.

"Pharmaceutically acceptable salt", as used herein, refers to an organic or inorganic salt which is useful in the treatment of a warm-blooded animal. Such salts can be acid or basic addition salts, depending on the nature of the compound of Formula (I). As used herein, "warm blooded animal" includes a mammal, including a member of the human, equine, porcine, bovine, murine, canine or feline species.

In the case of an acidic moiety in a compound of Formula (I), a salt may be formed by treatment of a compound of Formula (I) with a basic compound, particularly an inorganic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine. An especially preferred salt is a sodium or potassium salt of a compound of Formula (I).

With respect to basic moieties, a salt is formed by the treatment of a compound of Formula (I) with an acidic compound, particularly an inorganic acid. Preferred inorganic salts of this type may include, for example, the hydrochloric, hydrobromic, hydroiodic, sulfuric, phosphoric or the like salts. Preferred organic salts of this type, may include, for example, salts formed with formic, acetic, succinic, citric, lactic, maleic, fumaric, palmitic, cholic, pamoic, mucic, d-glutamic, d-camphoric, glutaric, glycolic, phthalic, tartaric, lauric, stearic, salicyclic, methanesulfonic, benzenesulfonic, para-toluenesulfonic, sorbic, puric, benzoic, cinnamic and the like organic acids. An especially preferred salt of this type is a hydrochloride or sulfate salt of a compound of Formula (I).

Also encompassed in the scope of the present invention are pharmaceutically acceptable esters of a carboxylic acid or hydroxyl containing group, including a metabolically labile ester or a prodrug form of a compound of Formula (I). A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. Esters of a compound of Formula (I), may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, $\alpha$-methoxyethyl, groups such as $\alpha$-(($C_1$-$C_4$)alkyloxy)ethyl; for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, $\alpha$-acetoxymethyl, etc.; ethoxycarbonyl-1-methyl; or $\alpha$-acyloxy-$\alpha$-substituted methyl groups, for example $\alpha$-acetoxyethyl.

Additionally, the compounds of the instant invention may have one or more asymmetrical carbon atoms and, therefore, may exist in stereoisomeric forms. All stereoisomers are intended to be included within the scope of the present invention. As used, "stereoisomer" or "stereoisomeric" refers to a compound which has the same molecular weight, chemical composition, and constitution as another, but with the atoms grouped such that their orientation in three-dimensional space is different. Such stereoisomers may exist as enantiomeric mixtures, diastereomers or may be resolved into individual stereoisomeric components (e.g. specific enantiomers) by methods familiar to one skilled in the art.

Further, the compounds of the invention may exist as crystalline solids which can be crystallized from common solvents such as ethanol, N,N-dimethylformamide, water, or the like. Thus, crystalline forms of the compounds of the invention may exist as solvates and/or hydrates of the parent compounds or their pharmaceutically acceptable salts. All of such forms likewise are to be construed as falling within the scope of the invention.

In another aspect, the compounds of the invention are useful for the therapeutic or prophylactic treatment of an inflammatory disease state in warm-blooded animals. For example, as noted, the compounds of the invention may be used as anti-inflammatory agents in an inflammatory disease, especially a mast-cell mediated disease, for example, asthma, allergy or pulmonary disorders.

While it may be possible to administer a compound of the invention alone, normally it will be present as an active ingredient in a pharmaceutical formulation. Thus, in one another embodiment of the invention, there is provided a formulation comprising a compound of Formula (I) in combination, admixture, or associated with a pharmaceutically acceptable carrier, diluent or excipient therefor.

The composition used in the noted therapeutic methods can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. Considerations for preparing appropriate formulations will be familiar to one skilled in the art and are described, for example, in Goodman and Gilman's: "The Pharmacological Basis of Therapeutics", 8th Ed., Pergamon Press, Gilman et al. eds. (1990); and "Remington's Pharmaceutical Sciences", 18th Ed., Mack Publishing Co., A. Gennaro, ed. (1990). Methods for administration are discussed therein, eg. for oral, topical, intravenous, intraperitoneal, or intramuscular administration. Pharmaceutically acceptable carriers, diluents, and excipients, likewise, are discussed therein. Typical carriers, diluents, and excipients may include water (for example, water for injection), buffers, lactose, starch, sucrose, and the like.

As noted, a compound of the invention can be administered orally, topically or parenterally (e.g. intravenously, intraperitoneally, intramuscularly, subcutaneously, etc.), or inhaled as a dry powder, aerosol, or mist, for pulmonary delivery, for example, in the treatment or prophylaxis of asthma. Such forms of the compounds of the invention may be administered by conventional means for creating aerosols or administering dry powder medications using devices such as for example, metered dose inhalers, nasal sprayers, dry powder inhaler, jet nebulizers, or ultrasonic nebulizers. Such devices optionally may be include a mouthpiece fitted around an orifice. In certain circumstances, it may be desirable to administer the desired compound of the invention by continuous infusion, such as through a continuous infusion pump, or using a transdermal delivery device, such as a patch.

Typically, when the compounds of the invention are to be used in the treatment of asthma or allergic rhinitis, they will be formulated as aerosols. The term "aerosol" includes any gas-borne suspended phase of a compound of the invention which is capable of being inhaled into the bronchioles or nasal passages. Specifically, aerosol includes a gas-borne suspension of droplets of the desired compound, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example.

For solutions used in making aerosols of the invention, the preferred range of concentration of the compounds of the invention is 0.1–100 milligrams (mg)/milliliter (mL), more preferably 0.1–30 mg/mL, and most preferably 1–10 mg/mL. Usually the solutions are buffered with a physiologically compatible buffer such as phosphate or bicarbonate. The usual pH range is from about 5 to about 9, preferably from about 6.5 to about 7.8, and more preferably from about 7.0 to about 7.6. Typically, sodium chloride is added to adjust the osmolarity to the physiological range, preferably within 10% of isotonic. Formulation of such solutions for creating aerosol inhalants is discussed, for example, in Remington's, supra; See, also, Ganderton and Johens, "Drug Delivery to the Respiratory Tract, Ellis Horwood (1987); Gonda, "Critical Review in Therapeutic Drug Carrier Systems" 6 273–313 (1990); and Raeburn et al. *J. Pharmacol. Toxicol. Methods.* 27 143–159 (1992).

Solutions of a compound of the invention may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

In one embodiment, devices of the present invention comprise solutions of the compounds of the invention connected to or contained within any of the conventional means for creating aerosols in asthma medication, such as metered dose inhalers, jet nebulizers, or ultrasonic nebulizers. Optionally such devices may include a mouthpiece fitted around the orifice.

In the treatment of allergic rhinitis, a device may comprise a solution of a compound of the instant invention in a nasal sprayer.

A dry powder comprising a compound of the invention, optionally with an excipient is another embodiment. This may be administered by a drug powder inhaler containing the described powder.

One skilled in the art will appreciate that the methods of the invention can be used in combination with other agents for the treatment of mast cell mediated inflammatory disorders, and particularly, asthma. β-Adrenergic agonists are especially useful in these combinations, because they provide symptomatic relief of the initial asthmatic response, whereas the compounds of the present invention may provide relief and be better suited to treating the late asthmatic response. Preferred β-adrenergic agonists in these solutions include any of the usual β-agonists employed for the relief of asthma, for example, albuterol, terbutaline, bitolterol mesylate, or the like.

Other agents useful in combination with the compounds of the invention include anticholinergics, such as ipratropium bromide, and antiinflammatory corticosteroids (adrenocortical steroids) such as beclomethasone, triamcinolone, flurisolide, or dexamethasone.

Further, a compound of the invention may be used in the treatment of immunomediated inflammatory skin conditions, such as urticaria and angioedema, eczematous dermatitis, and hyperproliferative skin disease, for example, psoriasis. In such cases, a compound of the invention could be administered topically so as treat the condition involved. Thus, by treating the animal with a topical preparation comprising a compound of the invention, one would expect a decrease in scaling, erythema, size of the plaques, pruritus and other symptoms associated with the skin condition. The dosage of medicament and the length of time required for treating each patient may vary, but one skilled in the art will recognize that variations may occur from patient to patient and adjust the treatment regimen accordingly.

Thus, in a further embodiment of the invention, there is provided a pharmaceutical preparation for topical application comprising a compound of the invention, typically in concentrations in the range of from about 0.001% to about 10%, in combination with a pharmaceutically acceptable carrier, excipient, or diluent therefor. Such topical preparations can be prepared by combining the compound of the invention with conventional pharmaceutical diluents and carriers commonly used in topical dry, liquid, cream and aerosol formulations. Ointment and creams may be formulated, for example, with an aqueous or oily base with the addition of suitable thickening and/or gelling agents. Such bases may include water and/or an oil such as a liquid paraffin or a vegetable oil such as peanut oil or castor oil. Thickening agents which may be used according to the characteristics of the base may include, for example, soft paraffin, aluminum stearate, cetostearyl alcohol, propylene glycol, polyethylene glycols, woolfat, hydrogenated lanolin, beeswax, and the like.

Lotions may be formulated with an aqueous or oily base and will include also, in general, one or more of the following: stabilizing agents emulsifying agents, dispersing agents, suspending agents, thickening agents, coloring agents, perfumes, and the like.

Powders may be formed with the aid of any suitable powder bases, for example, talc, lactose, starch and the like. Drops may be formulated with an aqueous base or non-aqueous base also comprising one or more dispersing agents, suspending agents solubilizing agents, and the like.

Any of the formulations of the invention may also include one or more preservatives or bacteriostatic agents, for example, methyl hydroxybenzoate, ethyl hydroxybenzoate, propyl hydroxybenzoate, chlorocresol, benzalkonium chlorides, and the like. Additionally, the formulations may contain other active ingredients such as antimicrobial agents, particularly antibiotics, anesthetics, analgesics and antipruritic agents.

The pharmaceutical formulations of the invention may be administered by parenteral or oral administration for prophylactic and/or therapeutic treatment. The pharmaceutical compositions can be administered in a variety of unit dosage forms depending on the method of administration. For example, unit dosage forms suitable for oral administration may include, powders, tablets, pills, capsules and dragées.

The pharmaceutical formulations can be administered intravenously. Therefore, the invention further provides formulations for intravenous administration which comprise a compound of the invention dissolved or suspended in a pharmaceutically acceptable carrier or diluent therefor. A variety of aqueous carriers can be used, for example, water, buffered water or other buffer solutions, saline, and the like. The resulting aqueous solutions can be packaged for use as is, or lyophilized, the lyophilized preparation being combined with a sterile aqueous solution prior to administration. The sterile aqueous solution for the lyophilized product can be packaged as a kit for use with the lyophilized formulation. The compositions can contain pharmaceutically acceptable substances to aid in administration and more closely mimic physiological conditions. Such substances, can include, for example, pH adjusting substances such as acids, bases or buffering agents, tonicity adjusting agents, wetting agents and the like. Such substances may include but are not limited to, for example, sodium hydroxide, hydrochloric acid, sulfuric acid, sodium acetate, sodium lactate, sodium chloride, potassium chloride, calcium chloride, sorbitan monolaurate, triethanolamine oleate, and the like or any other means familiar to one skilled in the art for maintaining pH at a desired level.

For solid formulations, carriers, diluents, and excipients known to one skilled in the art may be used. Such carriers, diluents and excipients may include, for example, mannitol, lactose, starch magnesium stearate, sodium saccharin, talcum, cellulose, glucose, sucrose, or other solid polyol sugar, magnesium carbonate, and the like. For oral administration, a pharmaceutically acceptable formulation is prepared by admixing any of the usual carrier, diluents, and excipients, such as those noted, with from about 0.1 to about 95% of a compound of the invention.

The compounds of Formula (I) may be prepared by a variety of methods familiar to one skilled in the art. For example, to prepare a compound of the formula:

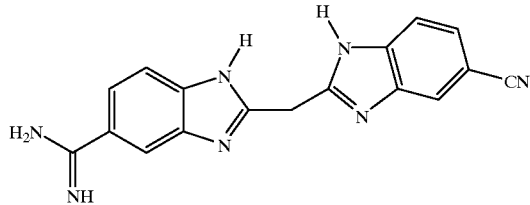
the following scheme was used:
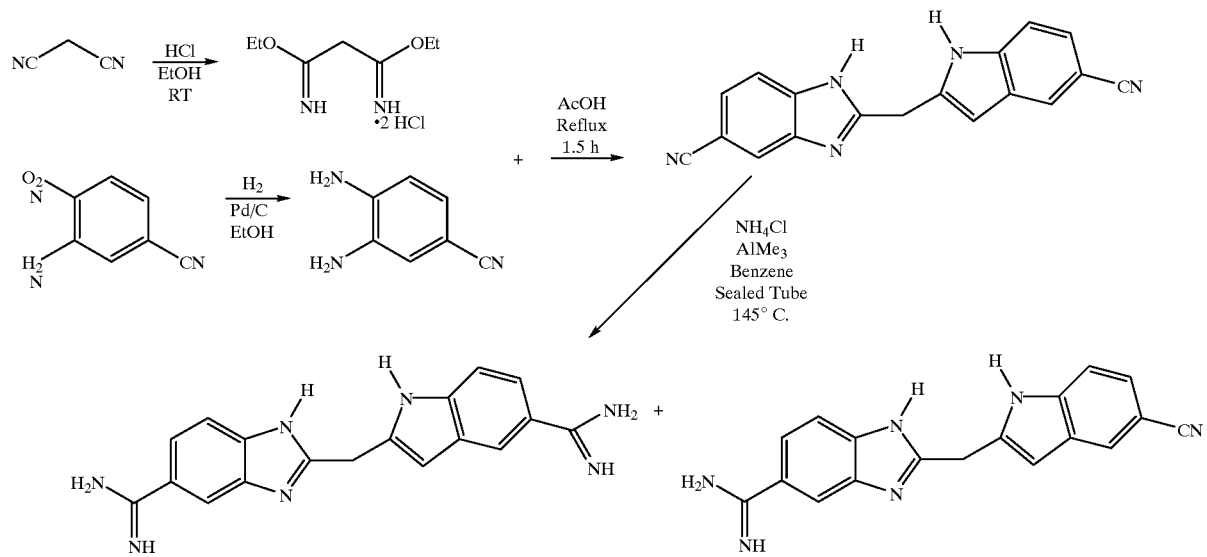
For those compounds which are amides, for example those of the following structure,
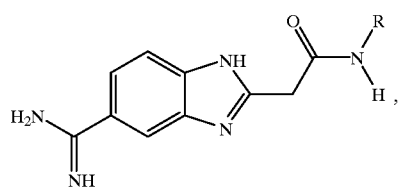
the following reaction scheme can be used:
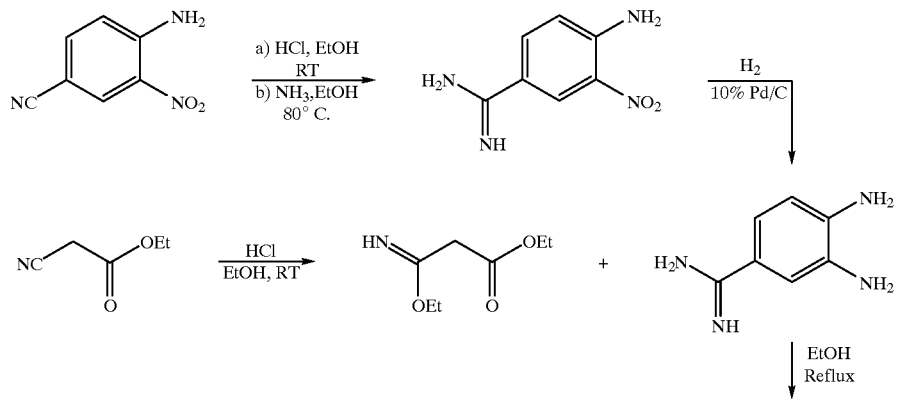

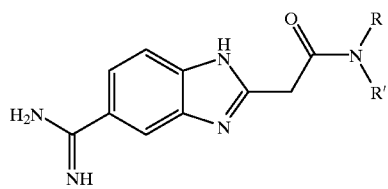 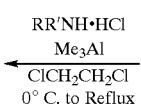 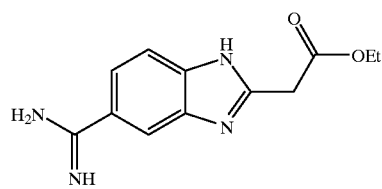
Compounds of Formula (I) in which Ar is an indole, for example of the formula:
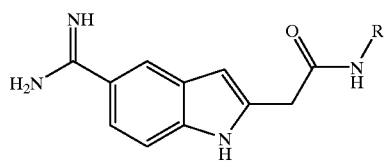
may be prepared according to the following general scheme:
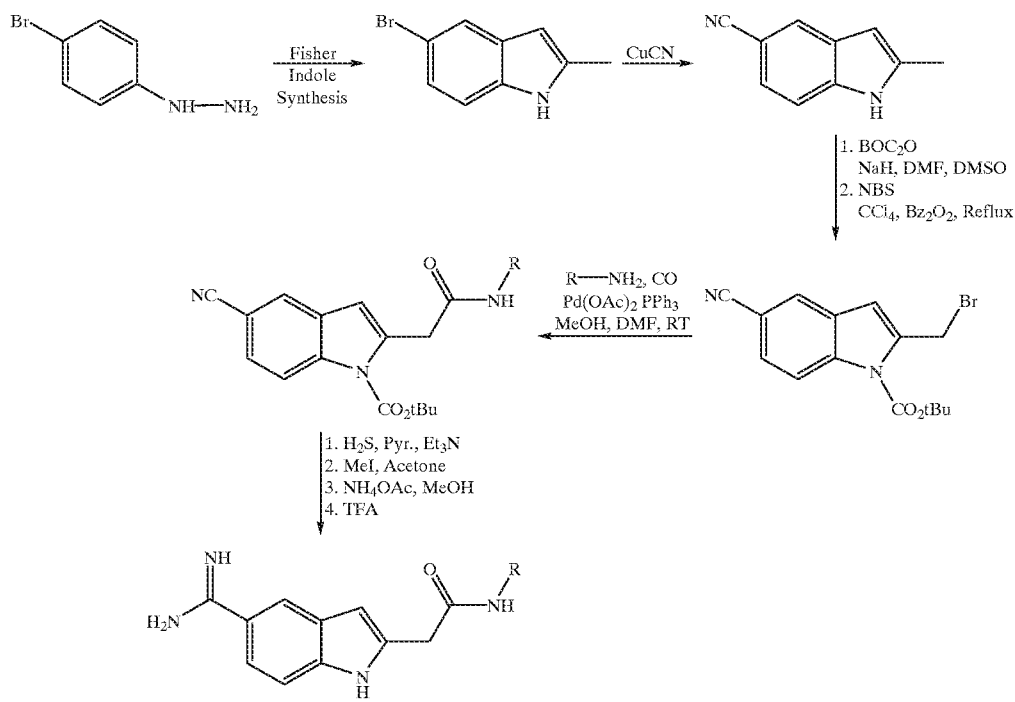

Those compounds of Formula (I) in which Ar is a benzothiophene moiety, that is, for example:
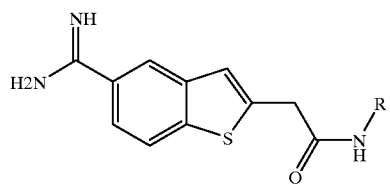
may be prepared by the following reaction scheme:
Those compounds of Formula (I) in which Ar is a naphthalene moiety, for example:
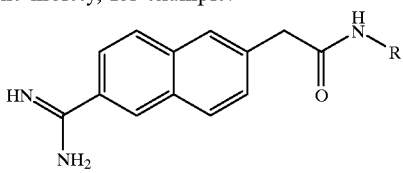
may be prepared in accordance with the following procedure:
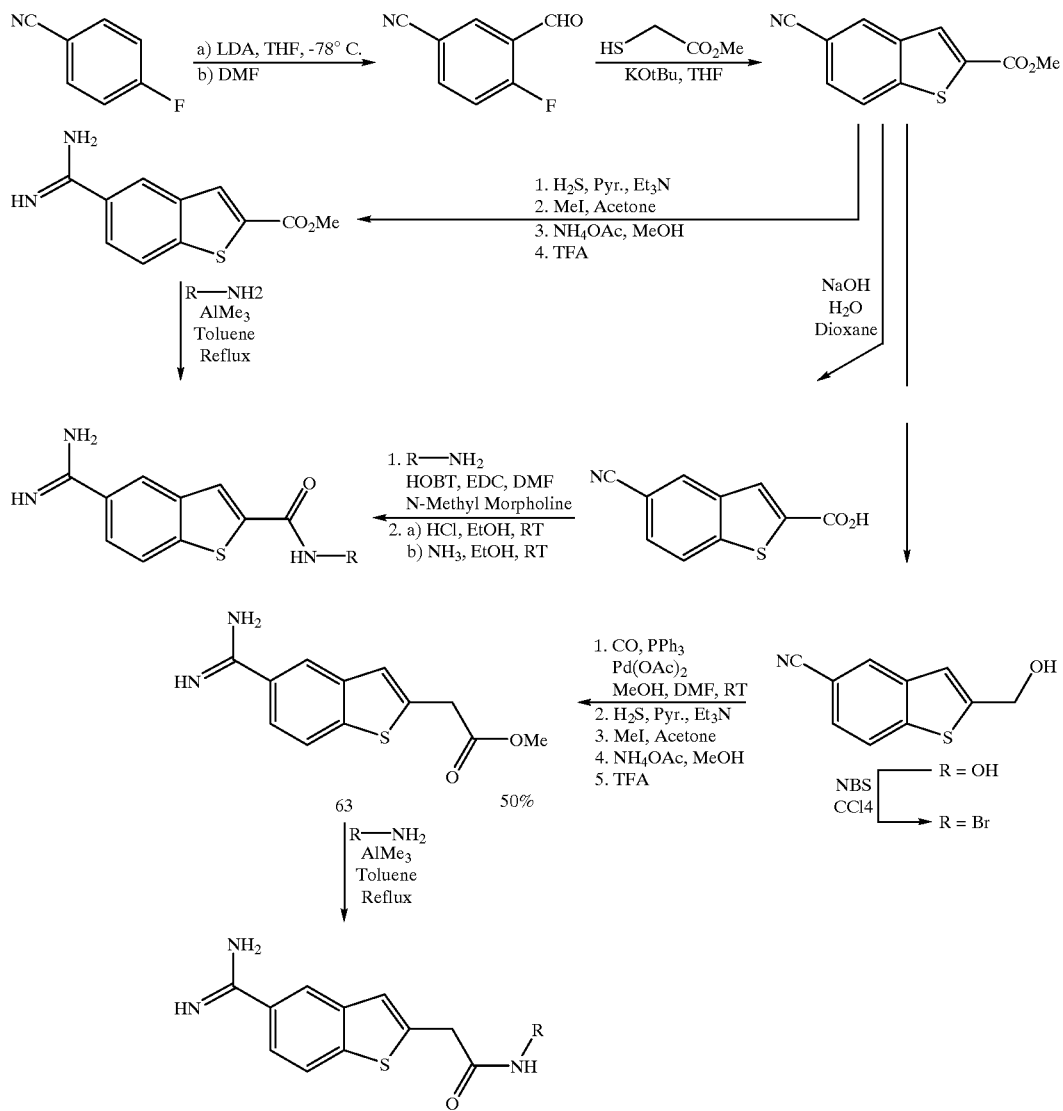

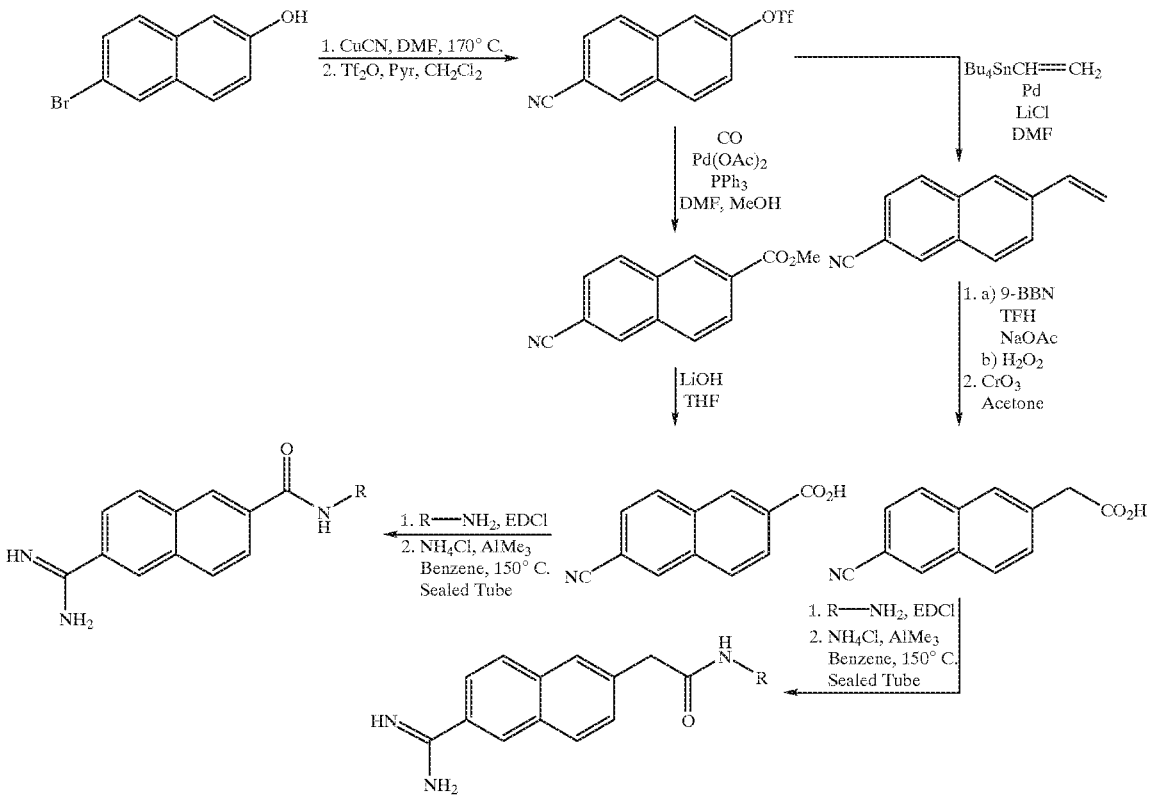

In a further optional step, if desired for an appropriate compound of Formula (I), the product of the reaction may be salified to prepare a pharmaceutically acceptable salt of the invention. Alternatively, and/or additionally, in a further embodiment for an appropriate compound of Formula (I), the product of the reaction may be esterified to prepare a pharmaceutically acceptable ester of the invention as previously defined.

The reactions used to prepare the compounds of Formula (I) may be carried out in any number of solvents in which the reactants may be mutually soluble, including, for example, tetrahydrofuran, benzene, toluene, chloroform, dichloromethane, N,N-dimethylformamide, ethyl ether, dioxane, acetonitrile, or the like. Generally the reaction is carried out at a temperature of between −80° and 150° C., preferably, however, at room temperature.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC using, for example, dilute trifluoroacetic acid in water, acetonitrile, or methanol mixtures as eluent), column chromatography, flash chromatography, radial chromatography, trituration, and the like.

In the preparation of the compounds of the invention, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, Ed., Plenum Press, New York, N.Y.; and "Protective Groups in Organic Synthesis," Greene, Ed., John Wiley & Sons, New York, NY (1981) for the teaching of protective groups which may be useful in the preparation of compounds of the present invention.

Alternate means beyond those described above for preparing the compounds of the invention will be apparent to one skilled in the art and the noted general procedures are not to be construed as limiting the invention.

Assay Procedures—$K_i$ Determinations of Proteases

Protease inhibition was assayed according to published procedures with minor modifications using various proteases and specific chromogenic peptide p-nitroanilide substrates. Assays were performed in Costar ultra-low cluster 96-well microtiter plate (Costar Corning Corp., Cambridge Mass.). Each protease was incubated with various concentrations of the test compound for 15 min. at 37° C. or as otherwise indicated, in specific assay buffer, and the residual activity was then measured by addition of the substrate. p-Nitroaniline produced by the proteolysis was determined by measuring the change in absorbance at 405 nm on a SpectraMAX 340 plate reader (Molecular devices, Sunnyvale, Calif.).

$K_1$ Determinations

1. The inhibition constant, $K_i$ is calculated from individual data points using the equation for a tight-binding inhibitor (See Beith, "Proteinase Inhibitors-Proceedings of 2nd Int. Res. Conference", Fritz, et al. eds., New York, p.4463–4469 (1974)):

$v_i/v_o=[((K_i'+[I]+[E]_o)^2-4[I]_o[E]_o)^{1/2}(K_i'+[I]_o-[E]_o)]/2[E]_o$ where $K_i'$ is apparent inhibition constant; $v_i$ and $v_o$ are the inhibited and uninhibited rates, respectively; $[I]_o$ and $[E]_o$ are the total concentrations of inhibitor and enzyme, respectively.

[note: $[E]_o$ is determined by active site titration of enzyme]

The $K_i$ values are obtained by correcting $K_i$ ' values for the effect of substrate concentration according to:

$$K_i = \frac{K_i'}{1+\frac{[S]}{K_m}}$$

(See Beith, *Biochem. Med.* 32, 387–397 (1984))

2. Other inhibition data ($K_i$>>$[E]_o$), the $K_i$ is calculated from using the equations for a competitive inhibitor:

$$K_i = \frac{IC_{50}}{1+\frac{[S]}{K_m}}$$

(See Segel, I. H. (1993) in "Enzyme Kinetics", Wiley Interscience, N.Y., pp. 106–107)

$IC_{50}$ is determined by fitting the individual inhibition data point to Sigmoid or four-parameter curve-fit equations.

A. Human Lung Tryptase

Human lung tryptase purchased from Cortex Biochem (San Leandro, Calif.) was purified further on a Superdex 200 gel-filtration column. The active-site concentration of the enzyme was determined by spectrophotometric titration with 4-nitrophenyl 4'-guanidinobenzoate according to Schwartz, et al., *J. Immunol.*, 114, 2304–2311 (1990). Tryptase activity was measured according to the procedures of Schwartz, et al., *J. Biol. Chem.*, 261, 7372–7379 (1986) (See also, Schwartz, L. B., *Methods In Enzymology*, 244, 88 (1994)) with minor modifications, using Tosyl-Gly-Pro-Arg-p-nitroanilide ("GPR-pNA", Sigma Chemical Co., St. Louis, Mo., T-1637) as a chromogenic substrate. The reaction was performed in 50 mM Tris-HCl, pH 8.0, containing 150 mM NaCl and 0.02% Triton X-100 at 37° C. in Costar ultra-low cluster 96-well microtiter plates (Costar Corning Corp., Cambridge, Mass.). The amount of pNA produced by tryptase was determined by measuring the change in absorbance at 405 nm on a SpectraMAX 340 plate reader (Molecular devices, Sunnyvale, Calif.). The $K_m$ for the substrate was determined by Lineweaver-Burk analysis from initial velocities of substrate hydrolysis. The inhibition assay was carried out in a total volume of 200 µL. Tryptase (30 µL-final concentration 1 nM) was incubated with various concentrations of sample compound (50 µL) to be tested in the above assay buffer for 5 min. The reaction was started by the addition of substrate GPR-pNA (40 µL-final concentration 320 µM), and the residual activity was measured after 15 min. of incubation. The inhibition constant, $K_i$, was determined by fitting the inhibition data to a two-site competitive binding equation using data analysis program GraphPad PRISM (GraphPad Software, Inc., San Diego, Calif.).

B. Human Neutrophil Elastase

Human Neutrophil elastase activity was determined by using pyroGlu-Pro-Val-pNA in 100 mM Tris-HCl, pH 8.3, 0.96 M NaCl, 1% BSA (See Kramps, et al. *Scand. J. Clin. Lab. Invest.* 43, 427–432 (1983)).

C. Bovine Pancreatic Trypsin

Bovine pancreatic Trypsin (TPCK-treated) activity was determined by using N-α-Benzoyl-L-Arg-pNA in 50 mM Tris-HCl, pH 8.2, 20 mM $CaCl_2$ (See Somorin, et al., *J. Biochem.* 85, 157–162 (1979)).

D. Bovine Pancreatic Chymotrypsin

Bovine Pancreatic Chymotrypsin activity was determined by using N-Suc-Ala-Ala-Pro-Phe-pNA in 100 mM Tris-HCl, pH 7.8, 10 mM $CaCl_2$ (See Delmar, et al., *J. Biochem.* 85, 157–162 (1979)).

E. Human Neutrophil Cathepsin G

Human Neutrophil Cathepsin G activity was determined by using N-Suc-Ala-Ala-Pro-Phe-pNA in 625 mM Tris-HCl, pH 7.5, 2.5 mM $MgCl_2$, 0.125% Brij 35 (See Groutas et al., *Arch. Biochem. Biophys.* 294, 144–146 (1992)).

F. Human Plasma Plasmin

Human plasma plasmin activity was determined by using Tosyl-Gly-Pro-Lys-pNA in 100 mM Tris-HCl, pH 7.4, 100 mM NaCl, 0.05% Triton X-100 (See Lottenberg, et al., *Meth. Enzymol.* 80, 341–361 (1981)).

G. Human Plasma Factor Xa

Human plasma factor Xa activity was determined by using N-Benzoyl-Ile-Glu-Gly-Arg-pNA in 50 mM Tris-HCl, pH 7.8, 200 mM NaCl, 0.05% BSA (See Lottenberg, et al. *Meth. Enzymol.* 80, 341–361 (1981)).

H. Human Plasma Thrombin

Human plasma thrombin activity was determined by using H-D-Phe-Pip-Arg-pNA in 50 mM Tris-HCl, pH 8.3, 100 mM NaCl, 1% BSA (See Lottenberg, et al., *Meth. Enzymol.* 80, 341–361 (1981)).

I. Human Plasma and r-tissue Kallikrein

Human plasma and r-tissue kallikrein activity were determined in 50 mM Tris-HCl1, pH 7.8, 200 mM NaCl, 0.05% BSA by using H-D-Prolyl-Phe-Arg-pNA and DL-Val-Leu-Arg-pNA, respectively (See Lottenberg, et al., *Meth. Enzymol.* 80, 341–361 (1981)).

The inhibition constant ($K_i$) of the test compounds against each proteolytic enzyme was determined according to Zitnik et al., *Biochem. Biophys. Res. Commun.* 232, 687–697 (1997)). The results are provided below.

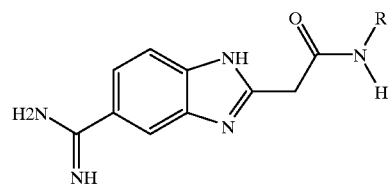

| R | Tryptase $K_i$ | Trypsin $K_i$ | Thrombin $K_i$ |
|---|---|---|---|
| H | 31.4 | — | — |
| $CH_3$ | 42.8 | — | — |
| $CH_2CH_3$ | 7.4 | — | — |
| $CH_2CH_2CH_3$ | 9.6 | — | — |
| Cyclohexyl | 36.9 | — | — |
| $CH_2CH_2$(4-Pyridyl) | 1.3 | — | — |
| 4-Piperidinyl(N-benzyl) | 1.7 | — | — |
| $CH_2$(4-Pyridyl) | 4.7 | — | — |
| 2-Napthyl | 5.2 | — | — |
| 2-Pyridyl | 1.2 | — | — |
| (4-OMe)Ph | 4.5 | — | — |
| $CH_2$Ph(3-Amino) | 0.49 | 7.5 | >100 |
| $CH_2$Ph(4-Amino) | 0.50 | 23.4 | 10.3 |
| (3-Amidino)Ph | 0.52 | 2.2 | >100 |
| (4-Amidino)Ph | 0.97 | 1.7 | >100 |
| (3-Amino)Ph | 0.29 | 14.2 | >100 |

-continued

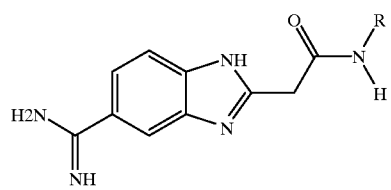

| R | Tryptase $K_i$ | Trypsin $K_i$ | Thrombin $K_i$ |
|---|---|---|---|
| (4-Amino)Ph | 3.0 | 14.2 | >100 |
| $CH_2Ph(4-CH_2NH_2)$ | 2.5 | — | — |
| (4-N(H)SO$_2$CH$_3$)Ph | 3.9 | — | — |
| (3-N(H)SO$_2$CH$_3$)Ph | 7.7 | — | — |
| (4-N(H)COCH$_3$)Ph | 6.4 | — | — |
| (4-SO$_2$NH$_2$)Ph | 2.2 | — | — |
| (4-OH)Ph | 2.7 | | |
| (3-OH)Ph | 0.57 | 8.7 | >100 |
| 6-Quinoline | 0.34 | 4.6 | >100 |
| 5-Indole | 0.81 | 21.8 | >100 |

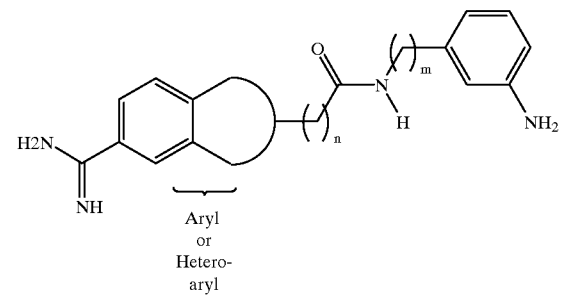

| Aryl Moiety | n | m | Tryptase Ki | Trypsin Ki | Thrombin Ki |
|---|---|---|---|---|---|
| Indole 5-carboxamidine | 1 | 0 | 0.39 | 4.0 | >100 |
| Benzthiophene 5-carboxamidine | 1 | 1 | 0.09 | 6.4 | >100 |
| Benzthiophene 5-carboxamidine | 0 | 0 | 0.52 | 14.0 | >100 |
| Benzthiophene 5-carboxamidine | 0 | 1 | 0.22 | 9.1 | >100 |
| Naphthalene (2,6-substitution) | 1 | 0 | 1.2 | 2.1 | >100 |
| Naphthalen (2,6-substitution) | 0 | 0 | 0.055 | 0.43 | >100 |
| Naphthalene (2,6-substitution) | 0 | 1 | 0.080 | 1.3 | >100 |

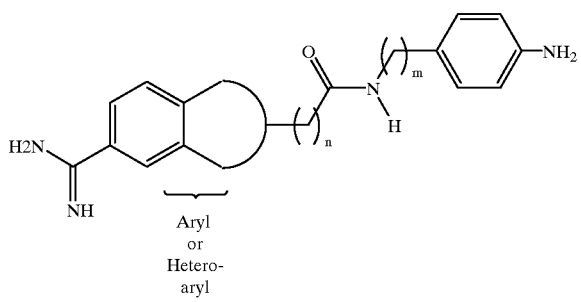

| Aryl Moiety | n | m | Tryptase $K_i$ | Trypsin $K_i$ | Thrombin $K_i$ |
|---|---|---|---|---|---|
| Indole 5-carboxamidine | 1 | 0 | 0.20 | 3.8 | >100 |
| Indole 5-carboxamidine | 1 | 1 | 0.44 | 3.4 | 65.0 |
| Benzthiophene 5-carboxamidine | 1 | 1 | 0.15 | 7.3 | >100 |
| Benzthiophene 5-carboxamidine | 0 | 1 | 0.44 | 8.8 | >100 |
| Benzothiophene 5-carboxamidine | 0 | 2 | 0.17 | 8.3 | >100 |
| Naphthalene 2,6-substitution | 0 | 1 | 0.21 | 0.59 | >100 |
| Naphthalene 2,6-substitution | 0 | 2 | 0.16 | 0.95 | >100 |

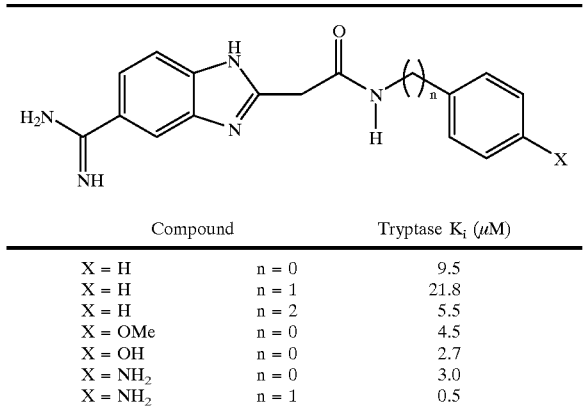

| Compound | | Tryptase $K_i$ ($\mu$M) |
|---|---|---|
| X = H | n = 0 | 9.5 |
| X = H | n = 1 | 21.8 |
| X = H | n = 2 | 5.5 |
| X = OMe | n = 0 | 4.5 |
| X = OH | n = 0 | 2.7 |
| X = NH$_2$ | n = 0 | 3.0 |
| X = NH$_2$ | n = 1 | 0.5 |

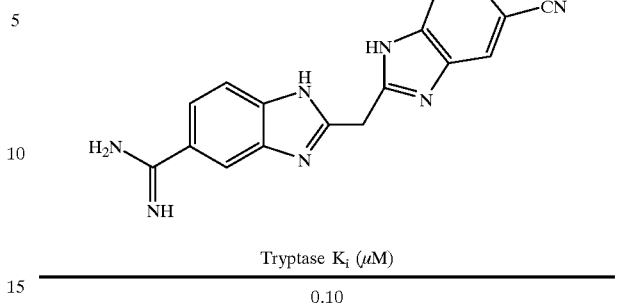

| Tryptase $K_i$ ($\mu$M) |
|---|
| 0.10 |

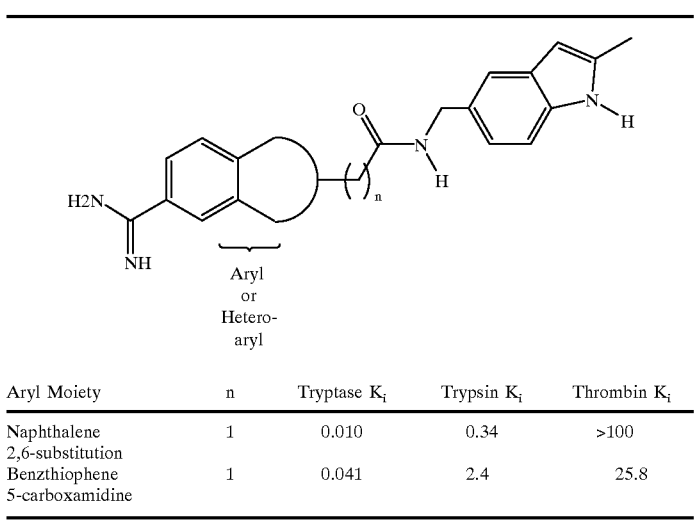

| Aryl Moiety | n | Tryptase $K_i$ | Trypsin $K_i$ | Thrombin $K_i$ |
|---|---|---|---|---|
| Naphthalene 2,6-substitution | 1 | 0.010 | 0.34 | >100 |
| Benzthiophene 5-carboxamidine | 1 | 0.041 | 2.4 | 25.8 |

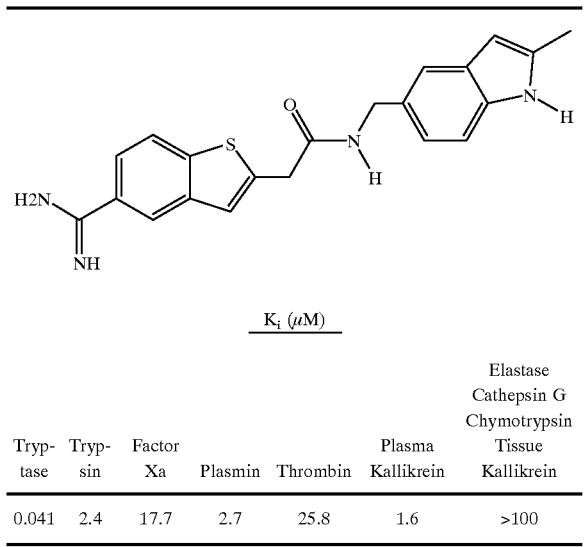

| $K_i$ ($\mu$M) | | | | | | |
|---|---|---|---|---|---|---|
| Tryptase | Trypsin | Factor Xa | Plasmin | Thrombin | Plasma Kallikrein | Elastase Cathepsin G Chymotrypsin Tissue Kallikrein |
| 0.041 | 2.4 | 17.7 | 2.7 | 25.8 | 1.6 | >100 |

It is to be understood that the above description is intended only to be illustrative of the invention and not restrictive. As will be apparent to one skilled in the art upon reading the description, other embodiments may be prepared and tested using other methods, reagents and procedures familiar to the skilled artisan. The scope of the invention, therefore, should not be determined solely based upon the specific teaching of the description. Instead, the scope of the invention should be determined based upon the teachings of the description along with reference to the appended claims and the full scope of equivalents to which the claims are entitled based upon the knowledge of one of ordinary skill in the art.

We claim:

1. A compound of the formula

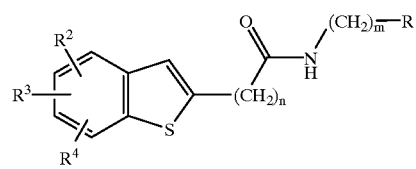

or a pharmaceutically acceptable salt, ester, or solvate thereof wherein:

$R^2$ is $(C_1-C_6)$ alkylthio, $(C_1-C_6)$ acyloxy, $(C_1-C_6)$ alkylaryl, $(C_1-C_6)$ alkyl-$SO_2NH$, $(C_1-C_6)$ alkyl CONH, $R^1HN$—C=NH—, $R^1HNCONH$—, —C≡N, $R^1HN(CH_2)v$-, —$SO_2NH_2$, —OH, —SH, —$CF_3$, —F, —Cl, —Br, —I, aryl, heteroaryl or —$NO_2$;

$R^3$ and $R^4$ are the same or different and represent hydrogen, $(C_1-C_6)$ alkyl, $(C_1-C_6)$ alkylthio, $(C_1-C_6)$ acyloxy, $(C_1-C_6)$ alkylaryl, $(C_1-C_6)$ alkyl-$SO_2NH$, $(C_1-C_6)$ alkyl CONH, —O$(C_1-C_6)$ alkyl, $R^1HN$—C=NH—, $R^1HNCONH$—, —C≡N, $R^1HN(CH_2)_v13$, —$SO_2NH_2$, —OH, —SH, —$CF_3$, —F, —Cl, —Br, —I, aryl, heteroaryl or —$NO_2$;

$R^1$ is hydrogen, $(C_1-C_4)$ alkyl-O—CO—, $(C_1-C_4)$ alkyl-O—, or —OH;

n is 1–10;

m is 0–10;

v is 0–6; and

R is hydrogen, $(C_1-C_4)$ alkyl, or $(C_3-C_8)$ cycloalkyl, provided that when m is 0, R is not hydrogen, or R is aryl or heteroaryl, each of which is unsubstituted or substituted with one, two or three groups selected from $(C_1-C_6)$ alkyl, $(C_1-C_6)$ alkylthio, $(C_1-C_6)$ acyloxy, $(C_1-C_6)$ alkylaryl, $(C_1-C_6)$ alkyl-$SO_2NH$, $(C_1-C_6)$ alkyl CONH, —O$(C_1-C_6)$ alkyl, $R^1HNCONH$—, —C≡N, $R^1HN(CH_2)_v$—, —OH, —SH, —$CF_3$, —F, —Cl, —Br, —I, or —$NO_2$, or R is a carbocyclic or heterocyclic ring with 5 to 7 members, each of which is unsubstituted or substituted with one, two or three groups selected from $(C_1-C_6)$ alkyl, $(C_1-C_6)$ alkylthio, $(C_1-C_6)$ acyloxy, $(C_1-C_6)$ alkylaryl, $(C_{1-C6})$ alkyl-$SO_2NH$, $(C_1-C_6)$ alkyl CONH, —O$(C_1-C_6)$ alkyl, $R^1HN$—C(=NH)—, $R^1HNCONH$—, —C≡N, $R^1HN(CH_2)_v$—, —$SO_2NH_2$, —OH, —SH, —$CF_3$, —F, —Cl, —Br, —I, aryl, heteroaryl or —$NO_2$.

2. A compound according to claim 1 in which $R^3$ and $R^4$ are hydrogen and $R^2$ is $R^1HN$—C(=NH)—.

3. A compound according to claim 1 which is 2-({N-[(3-aminophenyl)methyl]carbamoyl}methyl)benzo[b]thiophene-5-carboxamidine.

4. A compound according to claim 1 which is 2-({N-[(4-aminophenyl)methyl]carbamoyl}methyl)benzo[b]thiophene-5-carboxamidine.

5. A compound according to claim 1 which is 2-({N-[(2-methylindol-5-yl)methyl]carbamoyl}methyl)benzo[b]thiophene-5-carboxamidine.

6. A formulation comprising a compound of claim 1.

7. A formulation comprising a compound of claim 2.

8. A method for treating an inflammatory response in a warm-blooded mammal, comprising administering to said mammal an amount of a compound of claim 1 which is effective to treat said response.

9. A method for treating a mast-cell mediated condition in a warm-blooded mammal, comprising administering to said mammal an amount of a compound of claim 1 which is effective to treat said condition.

10. A method according to claim 9 in which the mast-cell mediated condition is tryptase-activated.

11. A method according to claim 9 in which the mast-cell mediated condition is an inflammatory disease.

12. A method according to claim 9 in which the mast-cell mediated condition is asthma, allergic rhinitis, rheumatoid arthritis, dermatological diseases, multiple sclerosis, conjunctivitis, inflammatory bowel disease, anaphylaxis, osteoarthritis, peptic ulcers, or cardiovascular disease.

* * * * *